United States Patent [19]

Kaplan

[11] Patent Number: 5,463,669
[45] Date of Patent: Oct. 31, 1995

[54] DENTAL X-RAY ALIGNMENT SYSTEM

[76] Inventor: Jerome I. Kaplan, 4417 N. Pennsylvania, Indianapolis, Ind. 46205

[21] Appl. No.: 302,524

[22] Filed: Sep. 8, 1994

[51] Int. Cl.$^6$ ........................................................ A61B 6/08
[52] U.S. Cl. ............................................. 378/205; 378/170
[58] Field of Search .................................. 378/205, 204, 378/167, 168, 170, 95

[56] References Cited

U.S. PATENT DOCUMENTS

| | | | |
|---|---|---|---|
| 4,223,228 | 9/1980 | Kaplan | 378/205 |
| 5,113,424 | 5/1992 | Burdea et al. | 378/170 |
| 5,150,056 | 9/1992 | Wilcock | 324/326 |

*Primary Examiner*—David P. Porta
*Attorney, Agent, or Firm*—Woodard, Emhardt, Naughton, Moriarty & McNett

[57] ABSTRACT

A simple, reliable, convenient and safe system for aiming a dental X-ray apparatus at an X-ray film plate. In the system of the present invention, magnetic field sensors, mounted on the dental X-ray apparatus, are used as a means of detecting the relative strength of a magnetic field of a magnet which is located next to an X-ray film plate within the mouth of a patient. By measuring and comparing the relative strengths of this magnetic field at each sensor, the system of the present invention can detect and indicate the condition of alignment or misalignment, including relative displacement in the x and y directions, as well as relative tilt about the x or y axes. Furthermore, the alignment system of the present invention can indicate misalignment of the X-ray film plate axes with the axes of the collimated X-ray beam. The present invention also provides a three-dimensional display by which the alignment or misalignment of the X-ray apparatus is conveniently indicated to the operator.

22 Claims, 4 Drawing Sheets

DENTAL X-RAY ALIGNMENT SYSTEM

BACKGROUND OF THE INVENTION

1. Technical Field of the Invention

The present invention relates generally to dental X-ray systems, and more particularly to dental X-ray systems providing for alignment of the X-ray cone with an X-ray film plate.

2. Description of the Prior Art

Dental X-ray photography has become an invaluable diagnostic aid to the dentist and today is often routinely performed in the dental office. However, difficulties are encountered in obtaining proper alignment of the dental X-ray apparatus with an X-ray film plate because the film plate is positioned intraorally and therefore cannot be seen by the dentist or technician during the aiming process. To avoid the problem of misalignment, a larger X-ray beam size is often used. This assures that the complete film plate will be exposed; however, it also increases the hazard caused by exposure of the patient to larger amounts of X-ray radiation.

Various X-ray alignment devices appear in the prior art which obtain proper positioning by mechanical means. U.S. Pat. No. 3,930,164 to Alexander discloses one such device that uses a centering rod to locate the center of the X-ray beam path and to position the subject accordingly. U.S. Pat. No. 4,057,733 to Hofmockel discloses an X-ray image intensifier which is mechanically mounted to the X-ray apparatus in such a manner that it can receive the emitted X-ray beam. The X-ray image received is reproduced on a video screen. In German Offenlegungsschrift No. 2,134,106 to Graf there is disclosed an X-ray film plate which is positioned on a frame mounted to the X-ray apparatus. These and similar devices using mechanical mounting means to obtain alignment have several disadvantages in that they are uncomfortable to the patient; they are inconvenient to use and difficult to position within the mouth; and they also pose a problem of sterilization. Further, the Alexander device is not adaptable for use in X-raying individual teeth within the mouth. Because the Hofmockel device uses a continuous beam, the overall X-ray exposure dosage to the patient is increased.

There are several prior art devices which use optics in order to obtain the desired positioning. U.S. Pat. No. 4,060,733 to Franke and U.S. Pat. No. 5,068,887 to Hughes both disclose a light beam which is reflected to illuminate the area at which the X-ray machine is pointed. In the field of dental X-rays, however, these are unsatisfactory devices because with dental X-rays, neither the film position nor the teeth are typically exposed to view. U.S. Pat. No. 3,790,803 to Phillips discloses another device that uses optics to obtain proper alignment. In Phillips, a beam of light is emitted from a fixed position on the X-ray apparatus. The beam of light is reflected from a fixed position relative to the X-ray film plate. In this manner, the device can indicate when there is proper alignment of the X-ray apparatus with the X-ray film plate. U.S. Pat. No. 4,012,638 to Altschuler discloses a device which applies optics specifically to the field of dental X-ray alignment. In Altschuler a plurality of infrared emitters and detectors are positioned on the X-ray apparatus. The X-ray film plate is positioned on a frame which extends outside the mouth and has an infrared reflective surface. When the infrared light emitted is reflected back and detected, alignment is indicated. Altschuler possesses many of the disadvantages of the mechanically mounted alignment devices, in that the film plate necessarily has to extend outside of the mouth. This attribute presents the problems of discomfort to the patient and of difficulty in positioning the film plate in its desired location within the mouth. The Altschuler device has the further disadvantage in that it does not determine the distance between the X-ray apparatus and the X-ray film plate. This information is desirable to properly adjust the size of the X-ray beam and therefore limit the amount of X-ray exposure to the patient. This distance is typically fixed in the mechanically mounted devices.

U.S. Pat. No. 4,223,228 to Kaplan discloses the prior art alignment system illustrated in FIG. 1. The X-ray source 10 includes a series of Hall effect sensors 11–14A and 11–14B on the X-ray cone. The X-ray film plate 43 to be exposed is placed within the patient's mouth 40 and held in place between teeth 44 by a tab 45. On the back of the X-ray film plate 43, there is a container 42 which holds a permanent magnet 41. The Hall effect sensors in the X-ray cone sense the magnetic field produced by the magnet 41. The signals from the Hall effect sensors are provided to a measurement and display means 30 via signal line 5. The display 32 includes a series of horizontal LEDs 33 and vertical LEDs 34, intersecting at the LED 37. The signals from the Hall effect sensors are processed such that illumination of the LEDs 33, 34 indicate the displacement of the X-ray source 10 relative to the film plate 43, with illumination of the LED 37 being the preferred position. The sensors 11B–14B are positioned far enough away from the magnet 41 so as to be unaffected by its magnetic field. Therefore, subtraction of the signals 11B–14B from the respective signals 11A–14A, correct for any effects of the Earth's magnetic field.

Although the X-ray alignment system of FIG. 1 represented a significant advance in the art at the time of invention, it nevertheless suffers from several disadvantages: the sensitivity of the Hall effect sensors impairs alignment when the X-ray cone is more than 3½ inches from the magnet; the low signal-to-noise ratio of the Hall effect sensors causes distortion error; the magnet 41 does produce effects on the sensors 11B–14B, thereby reducing the effectiveness of the correction for the Earth's magnetic field; while position of the X-ray film plate can be aligned with the X-ray cone, the angular orientation of the film plate relative to the X-ray cone cannot be measured or corrected; and the LED display is difficult for an operator to use and does not allow for display of angular orientation error. There is therefore a need in the prior art for a dental X-ray alignment system which overcomes any or all of these limitations. The present invention is directed towards meeting those needs.

SUMMARY OF THE INVENTION

The present invention is a simple, reliable, convenient and safe system for aiming a dental X-ray apparatus at an X-ray film plate. In the system of the present invention, magnetic field sensors, mounted on the dental X-ray apparatus, are used as a means of detecting the relative strength of a magnetic field of a magnet which is located in a known relationship to an X-ray film plate within the mouth of a patient. By measuring and comparing the relative strengths of this magnetic field at each sensor, the system of the present invention can detect and indicate the condition of alignment or misalignment, including relative displacement in the x and y directions, as well as relative tilt about the x or y axes. Furthermore, the alignment system of the present invention can indicate misalignment of the X-ray film plate axes with the axes of the collimated X-ray beam. The present invention also provides a virtual three-dimensional display by which the alignment or misalignment of the X-ray apparatus is conveniently indicated to the operator.

In one form of the invention, a dental X-ray alignment system for aiming a dental X-ray apparatus at an X-ray receiving device is disclosed, comprising a magnet, magnet positioning means for maintaining the magnet in a fixed relation with the X-ray receiving device, a plurality of first magnetic field strength detectors mounted in a fixed relation to the dental X-ray apparatus, measurement means operatively coupled to the first detectors for measuring a magnetic field strength of the magnet at a location of each of the first detectors, and processing means operatively coupled to the measurement means for calculating misalignment of the dental X-ray apparatus with the X-ray receiving device in at least two linear dimensions and at least two angular dimensions.

In another form of the invention, a method of correcting misalignment of a dental X-ray apparatus with respect to an X-ray receiving device is disclosed, comprising the steps of:

(a) positioning a magnet in a fixed relation with the X-ray receiving device;

(b) measuring a magnetic field strength of the magnet at a first plurality of locations; and (c) calculating the misalignment of the dental X-ray apparatus with the X-ray receiving device in at least two linear dimensions and at least two angular dimensions from the measured magnetic field strength.

It is therefore an object of the present invention to overcome the limitations inherent in the prior art devices. Further objects and advantages of the present invention will become more apparent from the following detailed description and accompanying drawings.

DESCRIPTION OF THE PREFERRED EMBODIMENT

Figure 1:
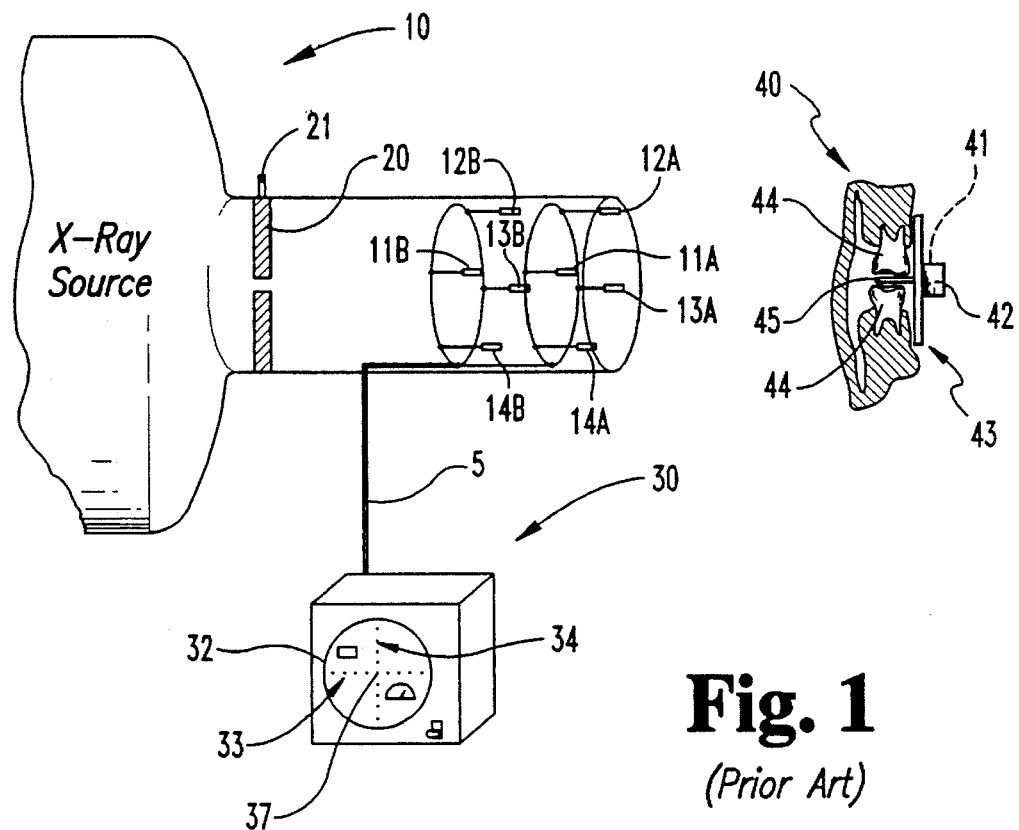
FIG. 1 is a schematic view of a prior art dental X-ray alignment system.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
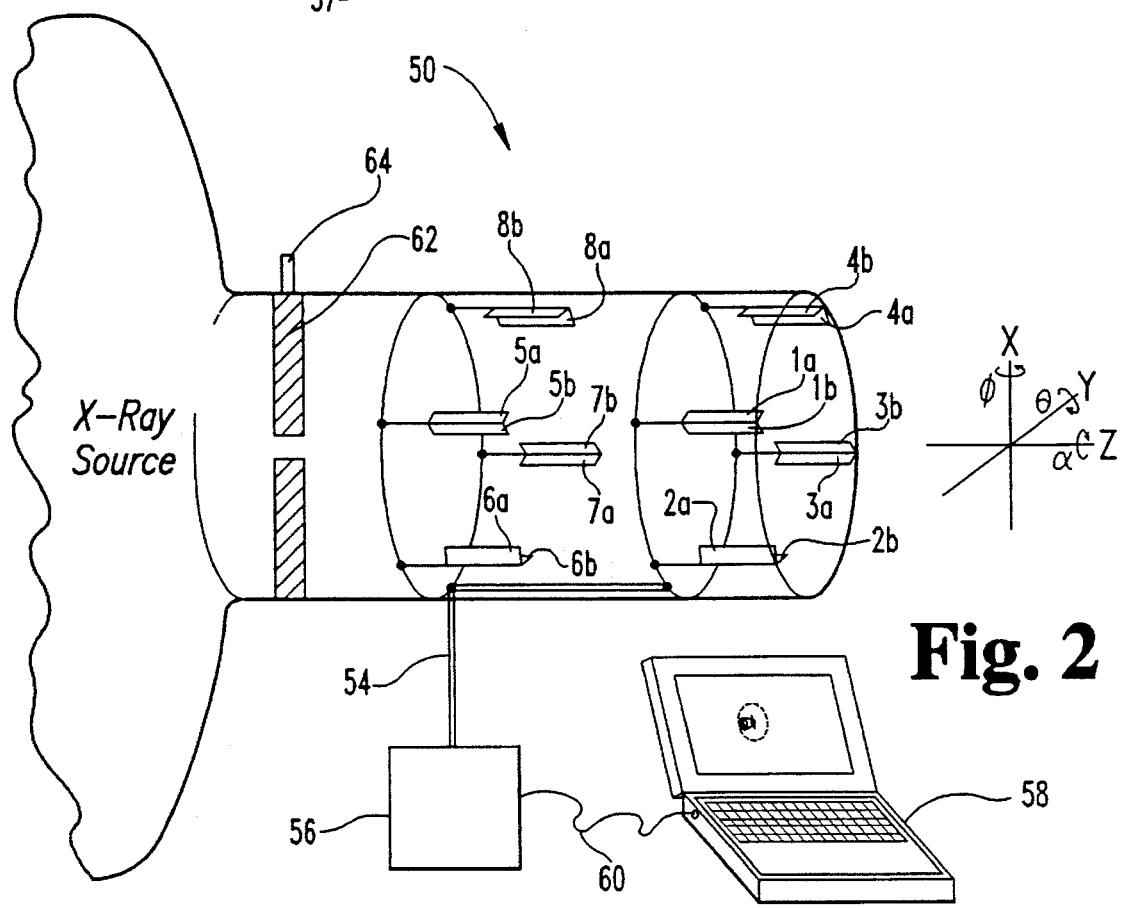
FIG. 2 is a schematic view of a dental X-ray alignment system of the present invention.

FIG. 2 schematically illustrates a preferred embodiment of the dental X-ray alignment system of the present invention, indicated generally at 50. The alignment system 50 comprises a first set of four detector pairs 1a–b, 2a–b, 3a–b and 4a–b. The first set of detectors are equally angularly spaced about the circumference of the cylindrical X-ray cone 52 of the dental X-ray apparatus. Detector pairs 1 and 3 are located on opposite sides of the X-ray cone 52 and are also positioned parallel to one another. Likewise, detector pairs 2 and 4 are located on opposite sides of X-ray cone 52 and positioned parallel to each other. For ease of illustration, the detector pairs 1–4 are shown rotated slightly about the z axis. However, detector pairs 1 and 3 lie on the y axis, while detector pairs 2 and 4 lie on the x axis. The detectors in each detector pair are positioned so as to detect only magnetic fields in the x and y directions and to be insensitive to magnetic fields lying only in the z direction. Additionally, each detector 1a–4a is oriented at a right angle from its respective detector 1b–4b.

A second set of detector pairs are also equally angularly spaced about the circumference of the cylindrical X-ray cone 52 and are located approximately 7 inches to the rear of the X-ray cone from the first set of detector pairs. Once again for ease of illustration, detector pairs 5a–b, 6a–b, 7a–b and 8a–b are shown slightly rotated, appearing not to be on a single horizontal and vertical plane in which they are actually positioned. Therefore, detector pairs 6 and 8 lie on the x axis, while detector pairs 5 and 7 lie on the y axis. Detector pairs 5–8 are also positioned so as to detect magnetic fields in the x and y directions only, and to be insensitive to magnetic fields lying entirely in the z direction. Each of the detectors 1–8 is a magnetoresistance detector, as will be explained in greater detail hereinbelow.

The various output signals from the detector pairs 1–8 are collected on signal lines 54 and input to electronic processing circuitry 56. Electronic processing circuitry 56 translates the analog electrical signal produced by each of the detectors into a periodically sampled digital representation of the analog signal. It will be appreciated by those skilled in the art that this may be accomplished by analog-to-digital processing circuitry as is well known in the art. This digital data is transferred to a processing device 58 via the line 60. As will be described in greater detail herein below, the data from detector pairs 1–8 is used to generate a graphical display on processor 58 in order to facilitate spacial alignment of the X-ray cone 52 with the X-ray film plate.

Each of the magnetoresistance detectors 1–8 is made from a thin film material which has the characteristic of dramatically changing its electrical resistance with changing magnetic field strength. A known voltage is therefore placed across each of the detectors and the current which thereby flows is measured by the electronic circuitry 56. The measured current from each of the detectors is periodically sampled by an analog-to-digital converter which produces a stream of digital output data indicative of the value of measured current for each of the detectors. This digital data is transmitted via line 60 to processor 58 which uses the measured current and the known voltage to calculate the instantaneous resistance of each of the detectors. Using the calculated resistance as an input value a look-up table stored in the processor 58 gives the magnetic field strength experienced by each of the detectors. As will be described in greater detail hereinbelow, such data from the detectors can be used to correct not only positioning error of the X-ray cone 52 in the x and y directions, but also tilting misalignment of the X-ray cone 52. The tilting misalignment is formed from three components: $\phi$, a measure of rotation about the x axis; $\theta$, a measure of rotation about the y axis; and $\propto$, a measure of rotation about the z axis.

Figure 3:
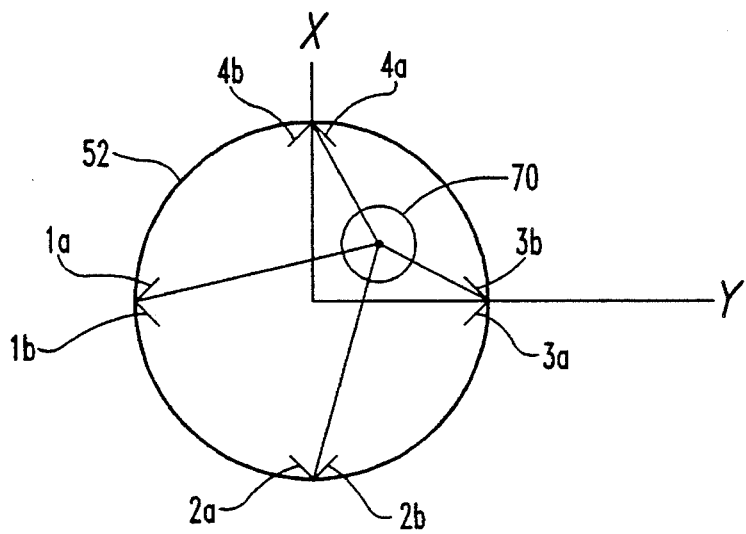
FIG. 3 is a schematic end view of the dental X-ray alignment system of the present invention with a magnet that is not rotated about the x or y axes.
Figure 4:
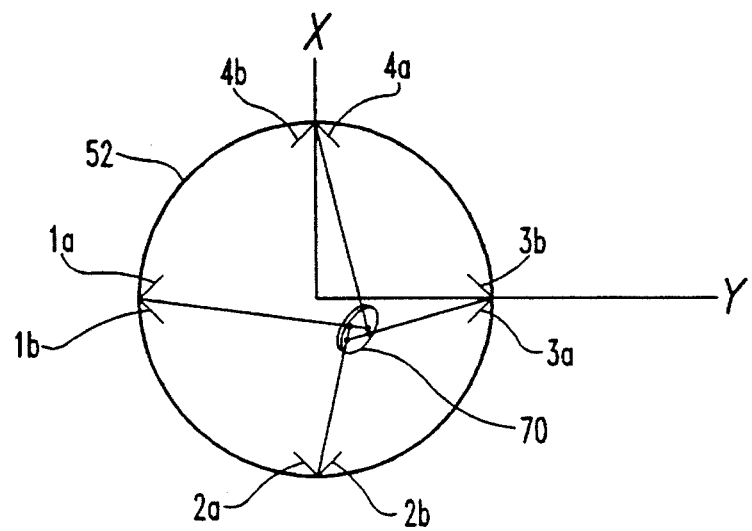
FIG. 4 is a schematic end view of the dental X-ray alignment system of the present invention with a magnet rotated about both the x and y axes.

Referring now to FIG. 3, the cylindrical X-ray cone 52 is viewed from its open end. If a cylindrically symmetric magnet is in the same plane as the (x, y) surface of the detector pairs 1–4, then magnetic field lines from the magnet 70 will be parallel to lines drawn from each detector pair to the center of the magnet 70, as illustrated schematically in FIG. 3. Thus, knowing the direction of the magnetic field lines at each detector (assuming the magnetic surface 70 is in the x-y plane) allows for an exact determination of the (x, y) position of the magnet 70 relative to the X-ray cone surface. Referring now to FIG. 4, if the magnet 70 is tilted from the x-y plane, the magnetic field lines will no longer be parallel to lines drawn from the center of the magnet 70 to each of the detector pairs. Thus, examination of each of the triangulation pairs (1, 2), (2, 3), (3, 4), and (4, 1) will provide different indicated site locations $(x_{12}, y_{12})$, $(x_{23}, y_{23})$, $(x_{34}, y_{34})$, and $(x_{41}, y_{41})$. It will be appreciated by those skilled in the art that these indicated locations can be averaged in order to give the approximate x,y location of the magnet 70 as:

$$(\bar{x}, \bar{y}) = \frac{x_{12} + x_{23} + x_{34} + x_{41}}{4}, \frac{y_{12} + y_{23} + y_{34} + y_{41}}{4} \quad (1)$$

After determining the approximate x,y location of the magnet 70, this information may be used to create a pictorial display on processor 58 which indicates the relative misalignment of the X-ray cone 52 with the X-ray film plate. The visual indication on the display of processor 58 may be used by the X-ray technician in aligning the X-ray cone 52 to the desired position, such that it is in alignment with the X-ray film plate. The preferred form of such display and its use by the X-ray operator will be described in greater detail hereinbelow.

Figure 5:
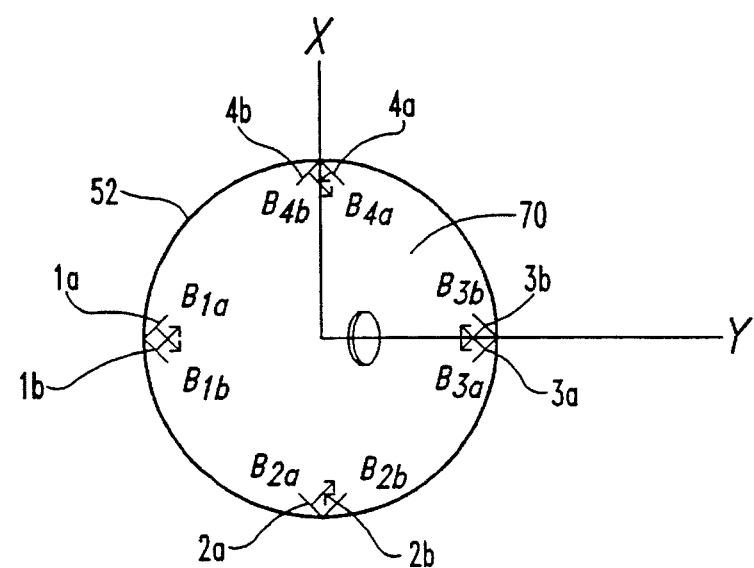
FIG. 5 is a schematic end view of the dental X-ray alignment system of the present invention with a magnet rotated about the x axis.

Even though the use of equation 1 above allows alignment of the X-ray cone 52 with the approximate x,y location of the magnet 70 when the magnet is tilted from the x-y plane, such tilt is an indication that the end of the X-ray cone 52 is not parallel to the magnet. Ideally, though, X-ray cone 52 should not only be aimed at the center of the magnet, but also be directed perpendicular thereto. Information from the detector pairs 1–8 is therefore used in order to produce an indication of the relative tilt of the magnet 70 about the x axis and about the y axis. Referring now to FIG. 5, the magnet 70 is shown positioned on the y axis but tilted away from the x-y plane. Each of the detector pairs 1–4 will produce a measure of the magnetic field strength perpendicular to the respective detector. Hence detector $1a$ produces a measure of the magnetic field strength labeled $B_{1a}$ and so forth. By comparing the magnetic field strength outputs from detector pairs located on opposite sides of the cone 52, it is possible to define two different measures of tilt $\theta$ (tilt about the y axis) and tilt $\phi$ (tilt about the x axis). For the first measure, the following definition is used:

$$\theta_1 = \frac{(B_{1b} + B_{3a} - B_{1a} - B_{3b})}{(B_{1b} + B_{3a} + B_{1a} + B_{3b})} \quad (2)$$

-continued
$$\phi_1 = \frac{(B_{2b} + B_{4a} - B_{2a} - B_{4b})}{(B_{2b} + B_{4a} + B_{2a} + B_{4b})} \quad (3)$$

The second measure is defined as follows:

$$\theta_2 = \frac{(B_{2b} + B_{2a} - B_{4a} - B_{4b})}{(B_{2b} + B_{2a} + B_{4a} + B_{4b})} \quad (4)$$

$$\phi_2 = \frac{(B_{3a} + B_{3b} - B_{1a} - B_{1b})}{(B_{3a} + B_{3b} + B_{1a} + B_{1b})} \quad (5)$$

The measures $\theta_1$, $\theta_2$, $\phi_1$ and $\phi_2$ measure different aspects of the tilt of the magnet 70. Therefore, their linear combination provides a good measure of the total tilt of the magnet 70.

$$\Delta\theta_0 = k_1\theta_1 + k_2\theta_2 \quad (6)$$

$$\Delta\phi_0 = k_1\phi_1 + k_2\phi_2 \quad (7)$$

$$k_1 + k_2 1 \quad (8)$$

The constants $k_1$ and $k_2$ are selected such that the tilt measurements $\Delta\theta_0$ and $\Delta\phi_0$ are relatively insensitive to the distance of the magnet 70 from the detector pairs 1–4. in a preferred embodiment, $k_1=\frac{1}{3}$ and $k_2=\frac{2}{3}$. Without this combination, the tilt parameters exhibit more variation with the detector-to-magnet distance along the z axis.

Finally, because a change in position, $\Delta x$, causes an apparent change in the tilt angle $\Delta\theta_0$, and a change in the tilt angle $\Delta\theta$ causes an apparent displacement x, the two motions can be connected by the coupled equations $$\Delta x = \bar{x} + b_1 \Delta\theta \quad (9)$$

$$\Delta\theta = b_3\Delta\theta_0 + b_2\Delta x$$

$$\Delta y = \bar{y} + b_1\Delta\phi \quad (10)$$

$$\Delta\phi = b_3\Delta\phi_0 + b_2\Delta y$$

where the constants $b_1$, $b_2$ and $b_3$ are a slowly varying function of the vertical distance z of the magnet 70 above the x-y plane of the detector pairs 1–4, and $\Delta x$, $\Delta y$, $\Delta\theta$ and $\Delta\phi$ are the parameters defining the visual display produced for the operator on the processor 58, as will be described in greater detail hereinbelow. The definition of $\Delta\theta_0$ and $\Delta\phi_0$ were chosen above such that $b_1$, $b_2$ and $b_3$ are relatively insensitive to changes in the distance z. Several combinations of $b_1$, $b_2$ and $b_3$ are determined empirically by varying the distance z above the detector palm 1–4 and then measuring $b_1$, $b_2$ and $b_3$ as a function of the approximate distance $\bar{z}$. This information is then compiled into a look-up table in processor 58 such that these constants can be determined once the approximate distance between the magnet 70 and the detector pairs 1–4 ($\bar{z}$) is known. The distance $\bar{z}$ can be determined from the detector pair measurements by the following equation:

$$\bar{B}(\bar{z}) = [B_{1a}^2 + B_{1b}^2 + B_{2a}^2 + B_{2b}^2 + B_{3a}^2 + B_{3b}^2 + B_{4a}^2 + B_{4b}^2]^{1/2} \quad (11)$$

The distance $\bar{z}$ can then be determined for any given $\bar{B}(\bar{z})$ from empirical data stored in a look-up table.

Figure 6:
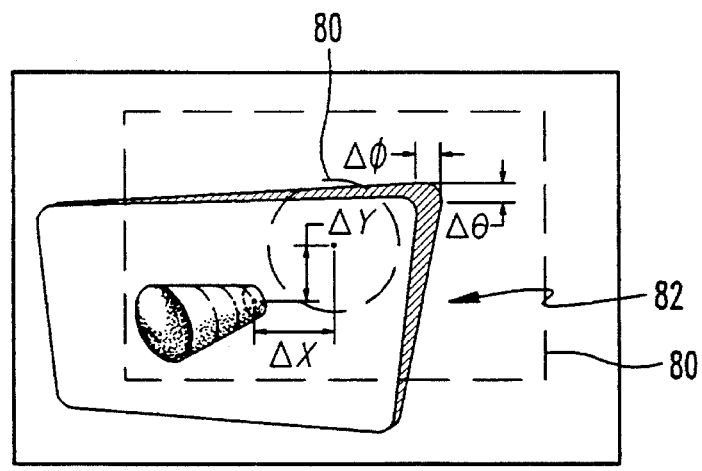
FIG. 6 is a first schematic view of a video display produced by the dental X-ray alignment system of the present invention.
Figure 7:
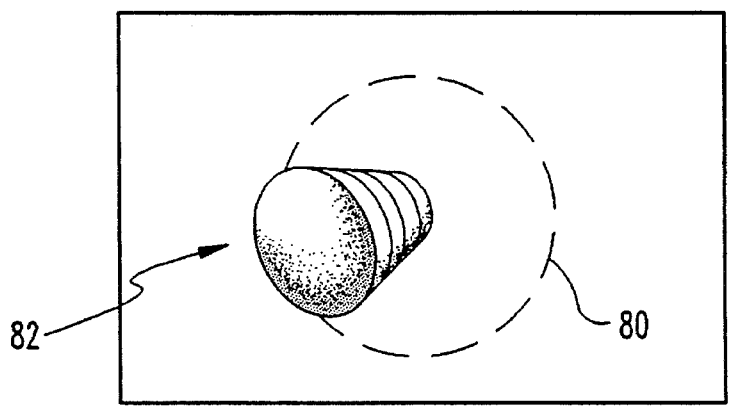
FIG. 7 is a second schematic view of a video display produced by the dental X-ray alignment system of the present invention.
Figure 8:
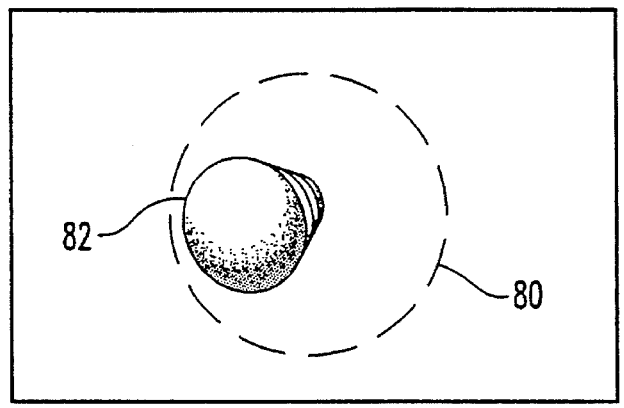
FIG. 8 is a third schematic view of a video display produced by the dental X-ray alignment system of the present invention.

FIGS. 6–8 illustrate an embodiment for the visual display of processor 58 which is used to give the operator of the X-ray equipment feedback on the relative positioning of the X-ray film plate with respect to the X-ray cone 52. The display consists of stationary hash marks 80 and a movable icon 82. The icon 82 is in the form of a box and truncated cone and is designed to give a three-dimensional impression of the relative positioning of the X-ray cone 52 with respect to the X-ray film plate/magnet 70. The detector measurements Δx and Δy are graphically displayed to the operator by the relative position of the icon 82 with respect to the hash marks 80, as indicated in FIG. 6. The display preferably exaggerates the relative distances so as to make the display easier to use. Furthermore, the tilt angles Δθ and Δφ are displayed by creating the appearance that the operator is not looking directly down upon three-dimensional icon 82. This display creates the sensation that the operator is hovering above the three-dimensional icon 82 and angular tilt of the magnet 52 in relation to the x-y plane creates the appearance of moving to one side of the icon 82, depending upon which direction (and about which axis) the tilt occurs. Therefore, increasing Δθ or Δφ causes increasing asymmetry in the icon 82, while decreasing Ae or Δφ causes the icon 82 to become more symmetrical. For example, in the illustration of FIG. 6 the X-ray film plate/magnet 70 is misaligned with the X-ray cone 52 in both the x and y directions as indicated by the misalignment of the icon 82 with the hash marks .80. Furthermore, the position of the X-ray cone 52 is tilted about both the x and y axes as indicated by the asymmetry of the icon 82. The graphical representation of FIG. 6 is displayed to the operator while the X-ray cone 52 is being positioned. Because of safety considerations, it is preferable that the gross adjustments made to the position of the X-ray cone 52 be made by hand so as to guarantee that the patient is not hit with the X-ray cone 52. Once the alignment system determines that the X-ray cone 52 is grossly aligned, the operator display automatically changes to the display illustrated in FIG..7, The system determines gross alignment using the following equation:

$$(\Delta x^2 + \Delta y^2 + \Delta\theta^2 \Delta\phi^2) < \text{Threshold 1} \tag{12}$$

where Threshold 1 is empirically determined.

Figure 9:
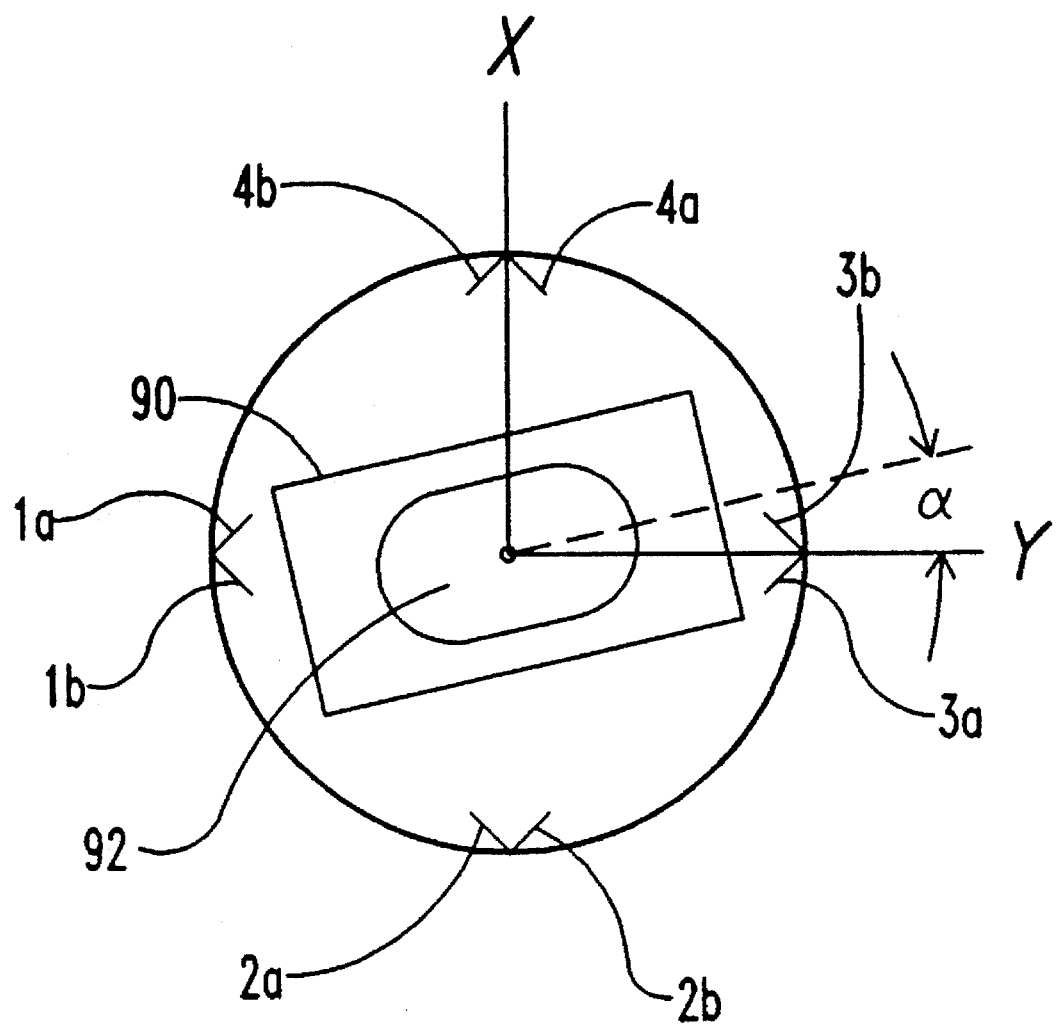
FIG. 9 is a schematic end view of the dental X-ray alignment system of the present invention with a magnet rotated about the z axis.

The switch to the close-up display of FIG. 7 allows for a larger display of finer adjustments. Such fine adjustments may be accomplished manually or with servomotors attached to the X-ray cone 52 and under the control of the processor 58. The display illustrated in FIG. 8 shows the icon 82 substantially aligned with the hash marks 80. This portion of the alignment process is terminated when $$(\Delta x^2 + \Delta y^2 + \Delta\theta^2 \Delta\phi^2) < \text{Threshold 2} \tag{13}$$

where Threshold 2<Threshold 1 and is also empirically determined. Even with complete correction of x-y positioning error, and the tilt angle errors e and φ, there still can be a positioning error of the X-ray film plate with respect to the X-ray cone 52 if the X-ray film plate is not symmetrical in shape. Referring now to FIG. 9, an X-ray film plate 90 is shown perfectly centered in the x-y plane and not tilted relative thereto. However, the long axis of the X-ray film plate 90 still is displaced from the y axis by an angle ∝ (tilted about the z axis). If the collimator device 62 (shown in FIG. 2) produces a rectangular X-ray beam, the X-ray film plate 90 will not be perfectly aligned with the X-ray beam because of the displacement ∝. This was not a problem in the prior art device of FIG. 1 in which a square X-ray film plate was used with a circular collimated X-ray beam. However, if a rectangular collimator is used with a rectangular X-ray film plate 90 (or a rectangular charge coupled device (CCD) as is known in the art), it is desirable that the collimated beam just cover the sensitive area of the X-ray film plate 90 in order to reduce the X-ray dosage penalty. The present invention therefore comprehends the use of a "race track" shaped magnet 92 which does not exhibit cylindrical symmetry. However, the "race track" shape of the magnet 92 is not so pronounced as to have a significant effect on the calculations in equations 1–11. Since the magnet 92 has asymmetrical axes, it allows for alignment of the rectangularly collimated X-ray beam with the long axis of the magnet 92, thereby correcting for any angle ∝ between the long magnet axis and the horizontal (y axis). In order to perform the necessary correction to eliminate the angle ∝, the magnetic field strength indicated by the detector 3b is compared to the magnetic field strength indicated by the detector 3a. When the magnet 92 is perfectly aligned with the y-axis (∝=0) then an equal magnetic field strength will be indicated by these two detectors. When detector 3b indicates a greater magnetic field strength than detector 3a the collimator 62 must be rotated counterclockwise. Conversely, when the detector 3a indicates a greater magnetic field strength than the detector 3b, the collimator 62 must be rotated clockwise. The processor 58 calculates the value of ∝ and then either instructs the operator to rotate the collimator 62 through ∝ degrees or, alternatively, a servomotor under the control of processor 58 may be used to move the collimator 62. When the angle ∝ has been reduced to a third empirically determined threshold, the X-ray film plate will be aligned with the rectangularly collimated X-ray beam. This results in minimum X-ray exposure by the patient and insures proper film coverage. When ∝<Threshold 3, a light signals the operator that the x-ray cone is aligned and an x-ray can be taken. The system will not allow an x-ray to be made unless alignment has been achieved. If, after alignment, the patient moves or the system otherwise becomes misaligned, the alignment display of FIG. 6 is reactivated and no x-ray may be taken until the system is re-aligned.

Referring once again to FIGS. 1 and 2, the correction for the effects of the Earth's magnetic field will now be explained. The signals produced by detector pairs 1–4 are corrected by subtracting the signals produced by detector pairs 5–8, respectively, in the electronics 56. Therefore, for example, the signal from detector 1a is reduced by the amount of the signal from detector 5a before the signal data is applied to processor 58. This correction is accurate insofar as the detector pairs 5–8 are sensitive only to the Earth's magnetic field, and not to the magnetic field produced by magnet 70. The field strength of a magnetic field produced by a magnet decreases in intensity with increasing distance from the detector to the magnetic field source. If r is the distance between the detector and the magnetic field source, the magnetic field strength decreases as $1/r^3$. The Earth's magnetic field correction detectors 11B–14B of the prior art apparatus of FIG. 1 relied on this decreasing magnetic field strength in order to insure that the detectors 11B–14B responded only to the Earth's magnetic field and not to the magnetic field produced by the magnet 41. However, in practice it is not practical to place the detectors 11B–14B far enough away from the magnet 41 so as to eliminate all effects of the magnet's magnetic field on these detectors. The correction produced by such a system, therefore, is only approximate and contains some amount of error. To overcome this problem, the system of the present invention as illustrated in FIG. 2 utilizes not only the $1/r^3$ relationship to insure independence of the detector pairs 5–8 from the magnet 70, but also a second method wherein the detector pairs 5–8 are sensitive only to magnetic fields in the x and y directions. The detector pairs 5–8 are placed far enough away from the magnet 70 such that the magnetic field produced by the magnet 70 in the vicinity of these detectors is almost entirely in the z direction. Therefore, the detector pairs 5–8, being sensitive only to magnetic fields in the x and y directions, are unaffected by the magnetic field produced by the magnet 70. In this way, the correction provided by the detector pairs 5–8 is almost entirely due to the magnetic field effects of the Earth's magnetic field, and is not corrupted by the magnetic field effects of the magnet 70. The apparatus of the present invention, therefore, provides a more accurate determination of the relative position of the X-ray film plate because of the more accurate correction for the effects of the Earth's magnetic field.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A dental X-ray alignment system for aiming a dental X-ray apparatus at an X-ray receiving device, comprising:
    a magnet;
    magnet positioning means for maintaining the magnet in a fixed relation with the X-ray receiving device;
    a plurality of first magnetic field strength detectors mounted in a fixed relation to the dental X-ray apparatus;
    measurement means operatively coupled to the first detectors for measuring a magnetic field strength of the magnet at a location of each of the first detectors; and
    processing means operatively coupled to the measurement means for calculating misalignment of the dental X-ray apparatus with the X-ray receiving device in at least two linear dimensions and at least two angular dimensions.

2. The dental X-ray alignment system of claim 1, further comprising:
    display means operatively coupled to the processing means for graphically displaying the misalignment of the dental X-ray apparatus with the X-ray receiving device.

3. The dental X-ray alignment system of claim 1, wherein the first detectors are sensitive only to components of magnetic field lines orthogonal to a longitudinal axis of the dental X-ray apparatus.

4. The dental X-ray alignment system of claim 1, wherein the first detectors are magnetoresistance devices.

5. The dental X-ray alignment system of claim 1, further comprising:
    a plurality of second magnetic field strength detectors mounted in a second fixed relation to the dental X-ray apparatus such that the second detectors are farther from the magnet than the first detectors, wherein the measurement means is operatively coupled to the second detectors for measuring a magnetic field strength of the Earth's magnetic field at each second detector location and the processing means corrects for the Earth's magnetic field when calculating the misalignment.

6. The dental X-ray alignment system of claim 5, wherein the second detectors are sensitive only to components of magnetic field lines orthogonal to the longitudinal axis of the dental X-ray apparatus.

7. The dental X-ray alignment system of claim 1, wherein the magnet is asymmetrical.

8. The dental X-ray alignment system of claim 7, wherein the magnet is race track shaped.

9. The dental X-ray alignment system of claim 7, wherein the processing means calculates misalignment of the dental X-ray apparatus with the X-ray receiving device in a third angular dimension.

10. The dental X-ray alignment system of claim 1, wherein the x-ray receiving device is a charge-coupled device.

11. The dental X-ray alignment system of claim 5, wherein:
    the first detectors are substantially equally angularly spaced along a first circumference of a first circle which is perpendicular to an X-ray beam emitted from the dental X-ray apparatus;
    the second detectors are substantially equally angularly spaced along a second circumference of a second circle which is perpendicular to the X-ray beam and spaced a distance away from the first circle; and
    the first and second circles have substantially the same radius.

12. The dental X-ray alignment system of claim 5, wherein the first fixed relation and the second fixed relation maintain the first and second detectors such that respective planes defined by a surface of each of the first and second detectors are substantially parallel to an X-ray beam emitted from the dental X-ray apparatus.

13. The dental X-ray alignment system of claim 11, wherein the first and second detectors are located in pairs at cardinal points of the first and second circles, respectively.

14. The dental X-ray alignment system of claim 13, wherein the detector pairs comprise two detectors positioned at a right angle to one another.

15. A method of correcting misalignment of a dental X-ray apparatus with respect to an X-ray receiving device, comprising the steps of:
    (a) positioning a magnet in a fixed relation with the X-ray receiving device;
    (b) measuring a magnetic field strength of the magnet at a first plurality of locations; and
    (c) calculating the misalignment of the dental X-ray apparatus with the X-ray receiving device in at least two linear dimensions and at least two angular dimensions from the measured magnetic field strength.

16. The method of claim 15, further comprising the step of:
    (d) graphically displaying the misalignment of the dental X-ray apparatus with the X-ray receiving device.

17. The method of claim 15, wherein step (b) comprises measuring only components of magnetic field lines orthogonal to a longitudinal axis of the dental X-ray apparatus.

18. The method of claim 15, further comprising the steps of:
    (e) measuring a magnetic field strength of the Earth's magnetic field at a second plurality of locations; and
    (f) correcting the measurement of step (b) using the measurement of step (e) in order to remove substantially all of an effect of the Earth's magnetic field prior to performing the calculation of step (c).

19. The method of claim 18, wherein step (e) comprises measuring only components of magnetic field lines orthogonal to a longitudinal axis of the X-ray apparatus.

20. The method of claim 15, wherein step (a) comprises positioning an asymmetrical magnet.

21. The method of claim 20, wherein step (c) further comprises calculating the misalignment of the dental X-ray apparatus with the X-ray receiving device in a third angular dimension.

22. The method of claim 18, wherein:
 step (b) comprises substantially equally angularly spacing a first plurality of detectors along a first circumference of a first circle which is perpendicular to an X-ray beam emitted from the dental X-ray apparatus; and
 step (e) comprises substantially equally angularly spacing a second plurality of detectors along a second circumference of a second circle which is perpendicular to the X-ray beam and spaced a distance away from the first circle, wherein the first and second circles have substantially the same radius.

* * * * *

UNITED STATES PATENT AND TRADEMARK OFFICE
CERTIFICATE OF CORRECTION

PATENT NO.  : 5,463,669

DATED       : October 31, 1995

INVENTOR(S) : Jerome I. Kaplan

It is certified that error appears in the above-identified patent and that said Letters Patent is hereby corrected as shown below:

In column 1, line 11, please delete "X-my" and insert in lieu thereof --X-ray--.

In column 1, line 35, please begin a new paragraph with "These".

In column 6, line 20, please insert -- = -- before "1".

In column 6, line 24, please delete "in" and insert in lieu thereof --In--.

In column 6, line 48, please delete "palm" and insert in lieu thereof --pairs--.

In column 6, line 57, please delete "$\bar{B}(\bar{z})$" and insert in lieu thereof --$\overline{B(\bar{z})}$--.

In column 6, line 60, please delete "$\overline{B(z)}$" and insert in lieu thereof --$\overline{B(\bar{z})}$--.

In column 7, line 16, please delete "Ae" and insert in lieu thereof --A$\theta$--.

In column 7, line 21, please delete ".80." and insert in lieu thereof --80.--.

In column 7, line 31, please delete "FIG..7" and insert in lieu thereof --FIG. 7--.

In column 7, line 35, please insert -- + -- after "$\Delta\theta^2$".

In column 7, line 45, please insert -- + -- after "$\Delta\theta^2$".

UNITED STATES PATENT AND TRADEMARK OFFICE
CERTIFICATE OF CORRECTION

PATENT NO.  : 5,463,669
DATED       : October 31, 1995
INVENTOR(S) : Jerome I. Kaplan It is certified that error appears in the above-indentified patent and that said Letters Patent is hereby corrected as shown below:

In column 7, line 48, please begin a new paragraph with "Even".
In column 7, line 49, please delete "e" and insert in lieu thereof --$\theta$--.
In column 8, line 23, please begin a new paragraph with "When".
In column 9, line 13, please delete the period before "drawings".

Signed and Sealed this

Fourth Day of June, 1996

Attest:

BRUCE LEHMAN

Attesting Officer    Commissioner of Patents and Trademarks